United States Patent [19]

Putman

[11] Patent Number: 4,953,406
[45] Date of Patent: Sep. 4, 1990

[54] RHEOMETER DIE ASSEMBLY

[76] Inventor: John B. Putman, 4638 Commodore Dr., Stow, Ohio 44224

[21] Appl. No.: 416,025

[22] Filed: Oct. 2, 1989

[51] Int. Cl.⁵ .............................................. G01N 3/24
[52] U.S. Cl. ......................................... 73/843; 374/48
[58] Field of Search .......................... 73/843, 60, 847; 374/46, 48, 53

[56] References Cited

U.S. PATENT DOCUMENTS 3,535,914 10/1970 Veith et al. ........................ 73/843 X
4,829,830 5/1989 Tosaki ................................ 374/48 X Primary Examiner—Jerry W. Myracle
Attorney, Agent, or Firm—Renner, Kenner, Greive, Bobak, Taylor & Weber

[57] ABSTRACT

A rheometer die assembly includes a lower oscillating or rotating die adapted for engagement with a stationary upper die. The lower die has an O-ring circumferentially positioned about a top surface thereof and in alignment with an annular planar sealing surface in the upper die. Engagement between the sealing surface and the O-ring defines a cavity between the two dies. A groove about a circumferential edge surface of the lower die is exposed when that die is received in a holder, such groove accepting the insertion of a tool for removing the die from the holder.

20 Claims, 2 Drawing Sheets

4,953,406

RHEOMETER DIE ASSEMBLY

TECHNICAL FIELD

The invention herein resides in the art of rheometers and viscometers employed for the testing of rubber compounds and, more particularly, to a die assembly employed thereby.

BACKGROUND ART

The use of rheometers and viscometers in rubber compounding and testing is extensively known. Reference herein will be made to rheometers generally, it being understood that the concept of the invention may be applied equally to both rheometers and viscometers. Rheometers typically comprise a pair of dies which mate with each other to form a cavity therebetween. An uncured rubber sample is placed within the cavity between the dies, the dies are heated to effect a cure, and one of the dies is caused to rotate or oscillate in a predetermined fashion. Such structure and technique is state-of-the-art and is presented to form a background for the invention herein.

The upper die is typically movable only in a vertical direction to make engagement with the lower die which, while not movable vertically, is connected to a motor or appropriate gearing to effectuate the desired rotational or oscillating motion. In the prior art, the lower die, often referred to as a rotor or rotating disc, is designed to allow the rubber to flow around it, making it necessary to pull the rubber from the rotor at the end of the rheometer test. In such embodiments, the rotor is actually encased by the rubber. Often, the rubber tears as it is being removed from the rotor and it becomes necessary to actually remove the rotor from the rheometer. This is not only time consuming, but also allows the upper and lower dies to cool down, delaying the testing operation and generating extra work effort.

In designs in which the rotor is not encased by the rubber, it is necessary that the rotating die be sealed with the stationary die to define a closed cavity. In the prior art, the moving die is sealed against the die holder, rather than directly against the mating die itself. Such seal is subjected to both axial and radial forces during the operation of the rheometer, causing such seal to experience rapid wear, necessitating frequent replacement. Indeed, the replacement of such seals has been found necessary on at least a daily basis, if not more frequently. Prior art seals, circumferential to the rotating disc, are difficult and time consuming to replace. Not only is the seal itself difficult to replace, but removal of the die to effectuate such replacement is also a time consuming and difficult task.

DISCLOSURE OF INVENTION

In light of the foregoing, it is a first aspect of the invention to provide a rheometer die assembly in which a seal is made between a moving and stationary die, and in which such seal is only subjected to radial forces.

Another aspect of the invention is the provision of a rheometer die assembly in which the seal between the dies can be quickly and easily replaced.

A further aspect of the invention is the provision of a rheometer die assembly in which only an interior cavity between the dies becomes encased in rubber, the remainder of the dies being sealed and protected from such encasement.

Yet an additional aspect of the invention is the provision of a rheometer die assembly in which the rotating or oscillating die can be quickly and easily removed from a die holder, being simply dropped into engagement with a drive mechanism through such holder.

An additional aspect of the invention is the provision of rheometer die assembly in which the seal between the dies is a simple O-ring, sealing on lateral edges thereof.

Yet a further aspect of the invention is the provision of a rheometer die assembly in which the seal between the dies is received by one of the dies in a snap-fit relation.

The foregoing and other aspects of the invention which will become apparent as the detailed description proceeds are achieved by a rheometer die assembly, comprising: an upper die having a horizontal surface; a lower die having a horizontal surface; and seal means interposed between said horizontal surfaces of said upper and lower dies for sealing said dies in contacting engagement with each other and defining a cavity therebetween.

Other aspects of the invention are obtained by a rheometer die assembly, comprising: a first die having a planar sealing surface; and a second die receiving a seal in a plane parallel to that of said sealing surface, said first and second dies being sealed with each other by engagement of said seal with said sealing surface.

Still further aspects of the invention are obtained by a rheometer die assembly, comprising: a lower die received within a die holder and having an O-ring seal received by a top horizontal surface thereof; and an upper die having a planar sealing surface in parallel and substantially congruent positional relationship with said O-ring seal, said upper and lower dies being sealed by engagement of said planar sealing surface with a circumferential surface of said O-ring.

DESCRIPTION OF DRAWINGS

For a complete understanding of the objects, techniques and structure of the invention reference should be made to the following detailed description and accompanying drawings wherein.

BEST MODE FOR CARRYING OUT THE INVENTION

Figure 1:
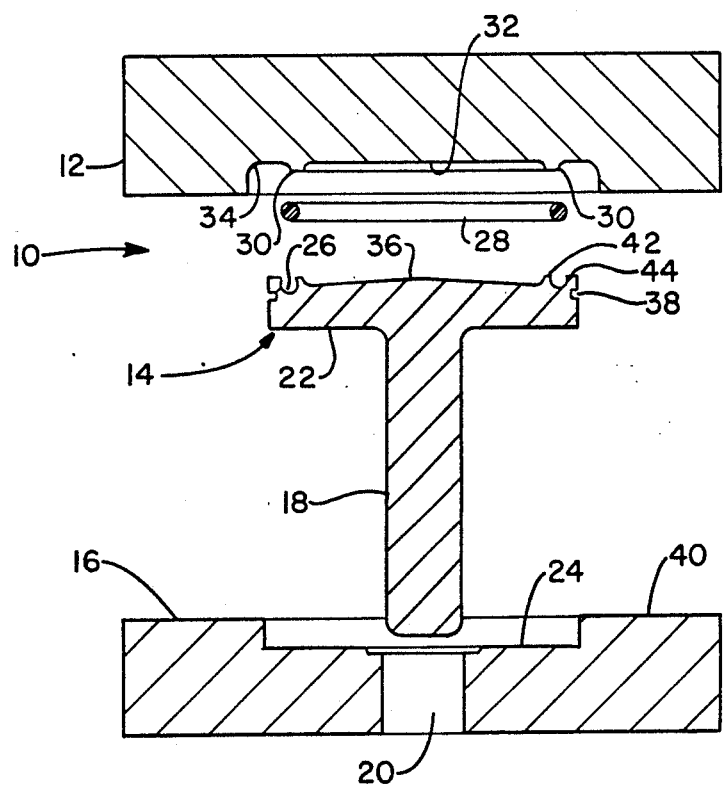
FIG. 1 is an assembly diagram of the structure of the rheometer die assembly of the invention.

Referring now to the drawings, it can be seen that a rheometer die according to the invention is designed generally by the number 10. An upper die 12 is brought into engagement with a lower die 14 to create a cavity therebetween for receipt of an uncured sample of a rubber compound or the like. In a preferred embodiment of the invention, the upper die 12 is not rotatable, but is vertically movable to be brought downwardly into engagement with the lower die 14 which, not vertically movable, is capable of rotation or oscillation.

A lower die holder 16 is provided for receiving the lower die 14. As shown, a shaft 18 extends downwardly from a lower surface of the lower die 14 and is adapted for receipt by a bore 20 passing through the lower die holder 16. As will be appreciated by those skilled in the art, the shaft 18 may then be received by a motor or gear box therebeneath for purposes of achieving rotational or oscillating motion. It will further be appreciated that the shaft 18 is simply a straight shaft, not including any means for being gripped or secured by the gear box or motor, such that it is received therein simply by gravity and may be quickly and easily removed. Indeed, any arbor, collar, or other suitable receiving means may be provided in association with the motor or gear housing for receipt of the shaft 18. For purposes of drive by the motor or gear assembly, the shaft 18 may be of square or rectangular cross section.

The lower die 14 also includes a die head 22 which is disc-shaped in configuration. This disc-shaped die head is adapted for receipt by a housed out receptacle or circular recess 24 of the lower die holder 16. The receptacle 24 comprises a partial depth bore which has an axis which is co-extensive with the axis of the bore 20, shaft 18, and disc 22.

An annular groove 26 is provided about the perimeter of a top surface of the lower die 14, such groove having a center concentric with the axis of the disc 22 and shaft 18. The groove 26 is semi-circular in cross section, preferably encompassing an arc greater than 180°, to define at least one lip protruding over the opening of the groove. As shown in FIG. 1, an inner lip 42 may extend outwardly over the opening of the groove 26, and an outer lip 44 may extend inwardly thereover. It will, of course, be appreciated that one of the lips may be so defined as to exit the groove vertically, without defining a lip protruding over the opening, such that the groove terminates its curvature at a 180° arc. In any event, it is preferred that at least one lip extend over the opening of the groove 26 for purposes of receiving and retaining an O-ring 28 therein. As shown, the O-ring 28 is congruent with the groove 26 and has a circular cross section having a radius substantially equal to that of the groove 26. Preferably, the O-ring 28 is temperature and wear resistant, made of a suitable material such as TFE. Because of the lip or lips 42, 44 extending over the groove 26, the ring 28 is snapped into the groove and held in place thereby.

The upper die 12 includes a planar sealing surface 30 which is congruent with the O-ring seal 28 and the groove 26. It will be appreciated that when the upper die 12 is brought into engagement with the lower die 14, the horizontal planar sealing surface 30 engages an upper lateral surface of the O-ring 28 which extends upwardly from the groove 26. Of course, the O-ring 28 also seals against the inner surfaces of the groove 26, particularly against the bottom surface thereof when the dies 12, 14 are brought together.

Figure 3:
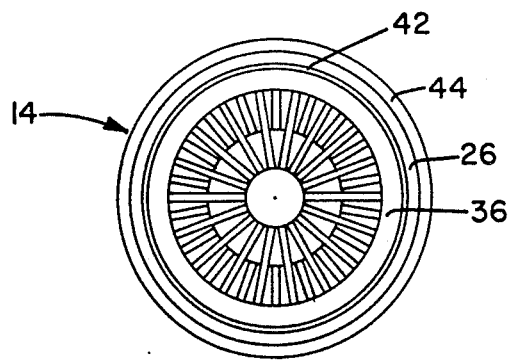
FIG. 3 is a top plan view of the bottom die assembly of the structure of FIG. 1.
Figure 2:
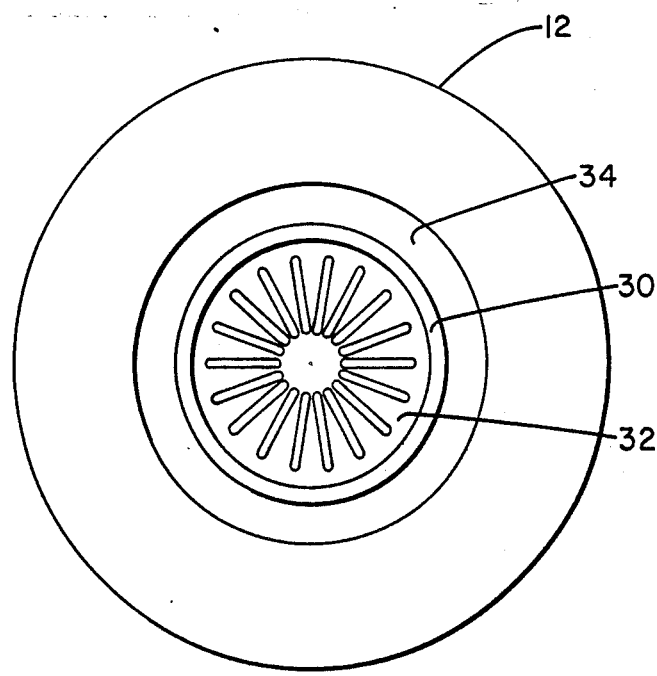
FIG. 2 is a bottom plan view of the upper die assembly of the structure of FIG. 1.

The sealing engagement of the O-ring 28 and surface 30 defines a cavity between the upper die plate 32 and the lower die plate 36, the same being characterized by plurality of radially extending ribs and recesses as shown in FIGS. 2 and 3, and as well known to those skilled in the art. Sealing engagement and definition of the cavity is further facilitated by the extension 34 of the upper die 12 beyond the circumferential edge of the lower die head 22.

A circumferential groove 38 passes about a circumferential edge of the die head 22 and is positioned above the bottom surface of the die head 22 such that the groove 38 intersects the plane of the top surface 40 of the lower die holder 16, or is positioned slightly thereabove. In either event, with the lower die 14 received within the receptacle 24 of the die holder 16, the circumferential groove 38 is either totally or partially exposed above the top surface 40 such that engagement with the groove 38 may be made with a blade or other thin implement to retract the die 14 from the holder 16. It will be appreciated that the die 14 is simply dropped into the holder 16 and that the shaft 18 is received, but not restrictingly engaged, by a motor or appropriate gear housing. Accordingly, the die may be quickly and easily removed and/or replaced. During such removal, replacement of the O-ring 28 may be quickly made by simply removing the old ring from the groove 26 and snapping a new one in its place.

It will further be appreciated that the die assembly 10 of the instant invention is contemplated for use in standard rheometer operations. Typically, the upper and lower dies will be heated by means of appropriate platens, or by direct interconnection of the upper die 12 and lower die holder 16 with a heating source. Appropriate thermocouple or other temperature sensors will, of course, be employed to monitor and maintain the temperature. Further, and as presented above, the lower die 14 is adapted for rotation and/or oscillation, while the upper die 12 is adapted only for vertical motion to make or break the seal with the O-ring 28. Of course, and as will be readily appreciated, the dies 12, 14 and holder 16 are all preferably constructed of an appropriate steel or metal composition suitable for the effective transfer of heat.

Thus it can be seen that the objects of the invention have been satisfied by the structure presented above. While in accordance with the patent statutes, only the best mode and preferred embodiment of the invention is presented and described in detail, it is to be understood that the invention is not limited thereto or thereby. Accordingly, for an appreciation of the true scope and breadth of the invention, reference should be made to following claims.

What is claimed is:

1. A rheometer die assembly, comprising:
    an upper die having a horizontal surface;
    a lower die having a horizontal surface; and
    seal means interposed between said horizontal surfaces of said upper and lower dies for sealing said dies in contacting engagement with each other and defining a cavity therebetween.

2. The rheometer die assembly according to claim 1, wherein said seal means comprises an O-ring.

3. The rheometer die assembly according to claim 2, wherein said O-ring has an inside surface and an outside surface, said O-ring contacting said horizontal surfaces of said upper and lower dies on opposing surfaces between said inside and outside surfaces.

4. The rheometer die assembly according to claim 3, wherein said O-ring has a circular cross section.

5. The rheometer die assembly according to claim 4, wherein said O-ring is removably received within a first groove in said lower die assembly.

6. The rheometer die assembly according to claim 5, wherein said first groove has a cross section which is semicircular, encompassing an arc exceeding 180° degrees.

7. The rheometer die assembly according to claim 5, wherein said upper die has a planar surface in substantial congruent alignment with said first groove.

8. The rheometer die assembly according to claim 1, wherein said lower die comprises a disc having a second groove circumferentially about an outer surface thereof.

9. The rheometer die assembly according to claim 8, wherein said lower die is removably received within a lower die holder, said second groove being exposed above a top surface of said die holder.

10. A rheometer die assembly, comprising:
a first die having a planar sealing surface; and
a second die receiving a seal in a plane parallel to that of said sealing surface, said first and second dies being sealed with each other by engagement of said seal with said sealing surface.

11. The rheometer die assembly as recited in claim 10, wherein said seal comprises an O-ring received within a first groove in a planar surface of said second die.

12. The rheometer die assembly as recited in claim 11, wherein said sealing surface comprises an annular ring substantially congruent with said O-ring.

13. The rheometer die assembly as recited in claim 12, wherein said second die comprises a plate having a second groove in an edge thereof.

14. The rheometer die assembly as recited in claim 13, wherein said second die is received by a holder having a top surface, said second groove being exposed above said top surface.

15. A rheometer die assembly, comprising:
a lower die received within a die holder and having an O-ring seal received by a top horizontal surface thereof; and
an upper die having a planar sealing surface in parallel and substantially congruent positional relationship with said O-ring seal, said upper and lower dies being sealed by engagement of said planar sealing surface with a lateral surface of said O-ring.

16. The rheometer die assembly according to claim 15, wherein said O-ring is received within a first circular groove in said top horizontal surface, said first circular groove being semicircular in cross section and defining an arc encompassing more than 180°.

17. The rheometer die assembly according to claim 15, wherein said lower die comprises a disc having a second groove about an outer circumference thereof.

18. The rheometer die assembly according to claim 17, wherein said second groove intersects a plane defined by said top horizontal surface.

19. The rheometer die assembly according to claim 17, wherein said second groove lies above said top horizontal surface.

20. The rheometer die assembly according to claim 15, wherein said lower die has a shaft extending from a bottom surface thereof, said shaft being received by a bore in said die holder, said shaft being unrestricted for vertical movement within said bore.

* * * * *